United States Patent [19]
Storz et al.

[11] Patent Number: 5,882,294
[45] Date of Patent: *Mar. 16, 1999

[54] MEDICAL INSTRUMENT HAVING A MANIPULATOR

[75] Inventors: Karl Storz, deceased, late of Tuttlingen, Germany, by Sybil Storz-Reling, executrix; Gérard Barki, Genéve, Switzerland

[73] Assignee: Karl Storz GmbH & Co., Germany

[ * ] Notice: This patent issued on a continued prosecution application filed under 37 CFR 1.53(d), and is subject to the twenty year patent term provisions of 35 U.S.C. 154(a)(2).

[21] Appl. No.: 765,664

[22] PCT Filed: Jul. 11, 1995

[86] PCT No.: PCT/DE95/00899

§ 371 Date: Jan. 10, 1997

§ 102(e) Date: Jan. 10, 1997

[87] PCT Pub. No.: WO96/01592

PCT Pub. Date: Jan. 25, 1996

[30]     Foreign Application Priority Data

Jul. 11, 1994 [DE] Germany .......................... 44 24 327.8

[51] Int. Cl.[6] ...................................................... A61B 1/04
[52] U.S. Cl. ........................................... 600/114; 604/271
[58] Field of Search ................................... 600/114, 117, 600/118, 102, 139, 146, 147, 148, 149, 150, 151; 604/271, 172

[56]                References Cited

U.S. PATENT DOCUMENTS 1,984,663  12/1934  Tatham .......................................... 32/27
4,616,648  10/1986  Simpson .
5,078,658   1/1992  Legg .
5,259,587  11/1993  D'Alessio et al. .

FOREIGN PATENT DOCUMENTS

| 0634146 | 1/1995 | European Pat. Off. . |
| 450345 | 3/1913 | France . |
| 2 681 919 | 4/1993 | France . |
| 44 898 | 10/1888 | Germany . |
| 549 080 | 4/1932 | Germany . |
| 838 938 | 5/1952 | Germany . |
| 494 022 | 9/1970 | Germany . |
| 3 122 061 | 2/1982 | Germany . |
| 3536747 | 4/1986 | Germany . |

*Primary Examiner*—Beverly M. Flanagan
*Attorney, Agent, or Firm*—St. Onge Steward Johnston & Reens LLC

[57]                ABSTRACT

The description relates to a medical and especially an endoscopic instrument having a manipulator with a guide channel on which are arranged at least one drive and at least one guide wheel or roller the peripheral surface of which can be engaged with the outer contour of an instrument part in such a way that this instrument part can be moved to and from along its longitudinal axis in relation to the manipulator. The instrument of the invention is distinguished in that, to fit different outside diameters of the instrument part to be moved, at least one of the wheels can be moved at least in the direction perpendicular to the guide channel and/or at least one of the wheels has an elastic coating on its outer periphery.

26 Claims, 3 Drawing Sheets

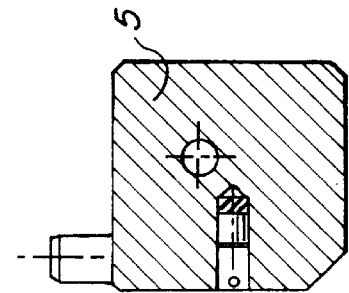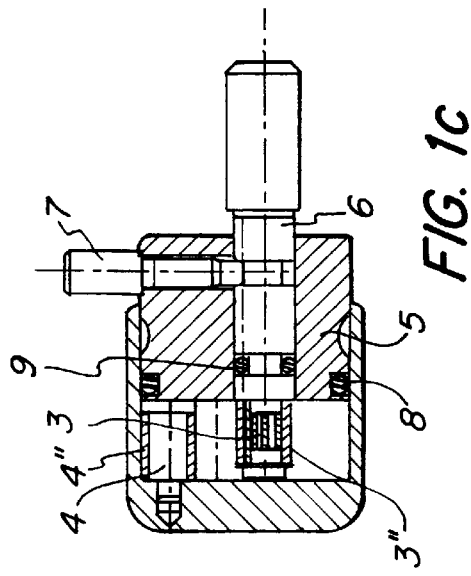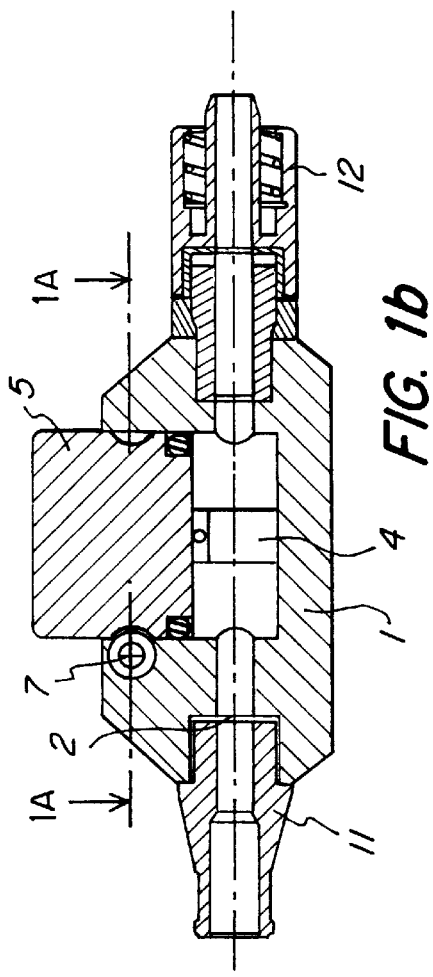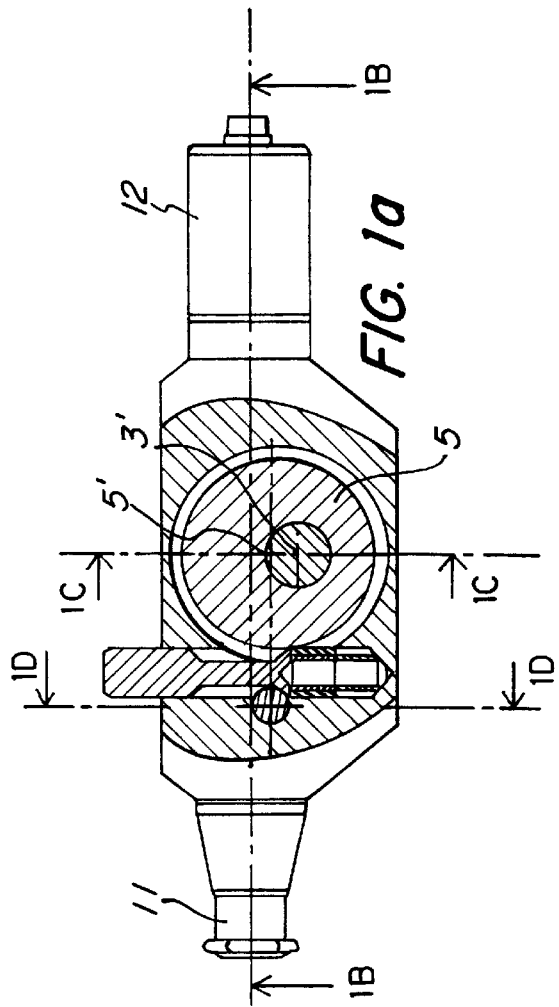

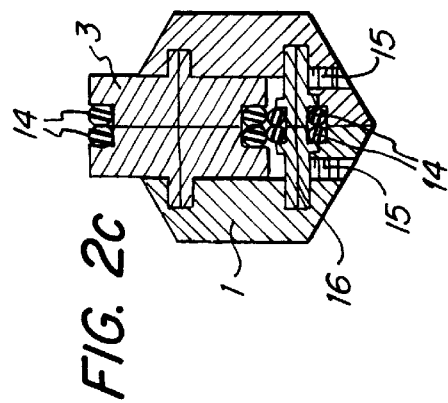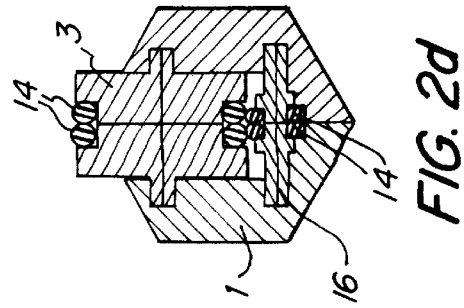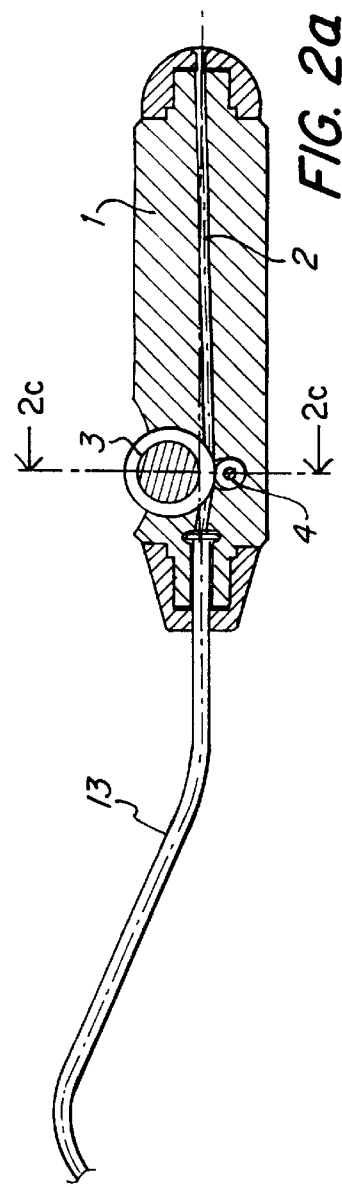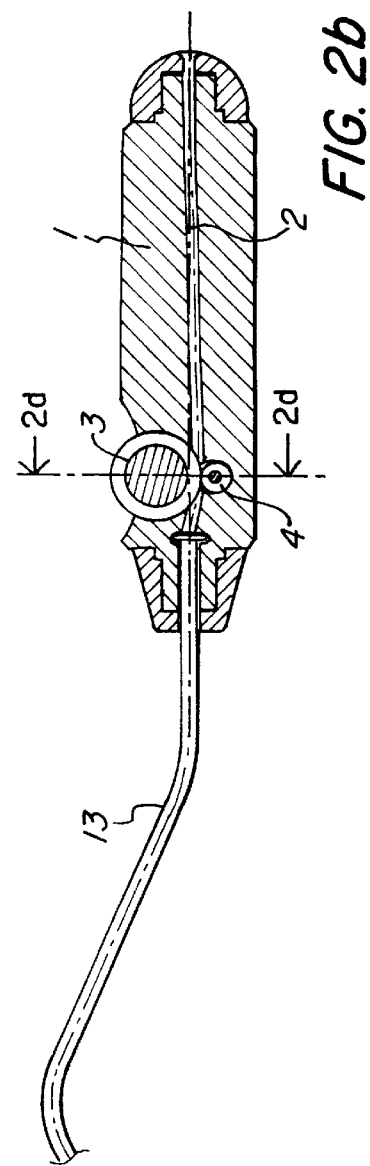

MEDICAL INSTRUMENT HAVING A MANIPULATOR

TECHNICAL FIELD

The present invention relates to a medical instrument and, in particular, to an endoscopic instrument having a manipulator according to the generic part of claim 1.

STATE OF THE ART

In a number of cases, it is necessary to move two, in particular, medical instruments precisely toward each other respectively one instrument part relative to the basic instrument. An example of this is moving tongs in a work channel of an endoscope shaft. Further examples are moving a laser fiber or a guide wire in a catheter or a flexible thin or ultra thin endoscope relative to the handpiece.

Known manipulators have a guide channel on which at least one driving wheel respectively driving roller and at least one guide wheel, preferably guide wheel whose perimeter area can be brought to engage with the outer contour of an instrument part in such a manner that this instrument part can be moved forward and backward in direction of its longitudinal axis to the manipulator. By way of illustration, manipulators for the relative movement of two instruments in direction of their longitudinal axis can be designed in such a manner that an (inner instrument) is inserted partially in a work channel of the other instrument (outer instrument).

In practice, it is frequently necessary to operate, i.e., move, instruments with different diameters successively in an endoscope or catheter. Furthermore, flexible endoscopes may have, i.a., due to fabrication tolerances, at least small variations in the outside diameter, which is quite detrimental to non-slip, preferably friction-free handling using known manipulators.

A manipulator which would permit handling instruments, preferably instruments parts having greatly different diameters has hitherto been unknown in the medical technology field.

Manipulators, like the aforedescribed ones, are moreover only suited for use in medicine in certain circumstances, because they are not easy to sterilize due to their complicated construction.

DESCRIPTION OF THE INVENTION

The object of the present invention is to provide a manipulator for moving an instrument part in relation to a basic manipulator body, preferably for the relative movement of two instruments which permits handling, preferably moving instruments having different diameters and, moreover, which is easy to sterilize.

A solution to this object according to the present invention is set forth in claim 1 hereto. Further improvements of the present invention, which can partly be viewed as independent inventions, are the subject matter of claim 2.

According to the present invention, an instrument having a manipulator is created which is distinguished by, for adaption to the different outside diameters, at least one of the wheels being moveable at least in the direction perpendicular to the guide channel and/or the outer contour of at least one of the wheels being provided with an elastic coating.

The moveability of at least one of the wheels respectively the rollers perpendicular to the moving direction also permits moving instruments, preferably instrument parts having greatly different diameters forward and backward successively with one and the same manipulator in the work channel of an instrument, by way of illustration an endoscope shaft.

If, on the other hand, it is only necessary to compensate fabrication variations in the outside diameters of, for instance, ultra thin flexible endoscopes for reliable and non-slip moving it suffices to design the perimeter of at least one of the wheels, preferably rollers elastically.

Invented further improvements respectively embodiments are set forth in claim 2 and the following claims.

The invented manipulator can, of course, be provided with multiple wheels, preferably rollers, for instance three rollers, for moving and guiding the instrument part to be moved, because particularly three rollers ensure reliable "straight guidance". The particularly simple embodiment described in claim 2 is a manipulator having two wheels positioned opposite each other.

In order to avoid slippage and/or in order to compensate differences in diameter due to fabrication, according to claim 3, it is preferable if at least the drive wheel or wheels are coated with a rubber-like elastic material in the region with which they engage with the outer contour of the to-be-moved instrument part permitting in this manner particularly precise work. The rubber-like material can, in particular, be silicone rubber (claim 4).

Claim 5 describes an especially preferred embodiment of the present invention in which the "large surface" contacting of the wheels of the to-be-handled instrument part ensures particularly reliable and precise advancing of the instrument to be moved.

In this embodiment, the perimeters of the wheels are provided with two-O-rings. Furthermore, the wheels are disposed in such a manner that two O-rings lie opposite each other respectively and that the O-rings enclose a gap through which the instrument part passes. The use of O-rings has the advantage that they can be easily exchanged and/or cleaned, preferably sterilized, which is especially advantageous in the field of medicine.

Another preferred embodiment of the present invention is set forth in claim 6:

In this embodiment, the moveable wheel for adaption to different diameters of the parts of the instrument is joined to a swiveling carrier in such a manner that the distance between the swivel axis thereof and the axis of rotation of this wheel does not equal zero. In other words, for the adaption of different instrument diameters, the moveable wheel is borne eccentrically on the swivel carrier.

The carrier can, in particular, be a disk which can be turned about its center axis and on which the axis of rotation of the wheel is placed eccentrically, with the wheel being moved by turning the disk (claim 7). Furthermore, it is preferred if the carrier has a circular outer contour in the cross sections that are perpendicular to the swivel axis and can be turned, in particular by hand, at least 360°. In this way, the carrier can be turned "to the left or the right" until the wheel joined to it eccentrically contacts the respective instrument to-be moved forward and backward in a sufficiently firm manner that the instrument can be moved without slippage.

An alternative embodiment is described in claim 9, in which, for adaption to the different diameters of the parts of instrument by moving one of the wheels, two screws are provided which act on the axis of this wheel, preferably the roller. In this embodiment, it is preferred if the axis of the moveable wheel is pretensioned by a spring in the opposite direction of the screw direction (claim 10).

Irregardless of the steering of the moveable wheel, according to claim 11, it is advantageous if the moveable wheel for adaption to the different instrument diameters is the drive wheel. Notably in this way, by turning, preferably swiveling the carrier, the contact pressure can be directly set in such a manner that a momentum sufficient for moving the instrument part can be transmitted and therewith difficult handling tasks can also be solved.

In addition, it is preferred if, according to the further improvement described in claim 12, the drive wheel has a substantially smaller diameter than the guide wheel or wheels.

Thereby it, notably the instrument, preferably the instrument part, can be moved precisely forward and backward, because a large angle of rotation of the drive wheel is required for small movements, with reliable guidance being ensured by the large guide wheel.

The invented instrument can be designed in a grat variety of ways:

By way of illustration, the wheels can be disposed in a handpiece which is provided with a channel for the to-be-moved instrument part. This embodiment is especially suited for handling, preferably moving thin flexible endoscopes (claim 13).

In a further improvement, the manipulator is provided at least on one side of the guide channel with a standard flange for connection to one of the instruments.

This standard flange can, by way of illustration, be a Luer-lock flange or an endoscope shaft flange. By means of this further improvement, the invented manipulator can be attached to existent catheters or endoscope shafts without needing to change, preferably adapt the latter in any manner.

The invented manipulator can, of course, be firmly connected to one of the instruments, i.e., to the basic body, preferably the manipulator can be integrated in an instrument, as by way of illustration in an endoscope shaft.

Irregardless of the aforedescribed details of the embodiment of the invented instrument it is advantageous especially for medical applications if the wheel carrier is attached in a detachable manner in a manipulator basic body (claim 18) and/ or the shaft of the drive wheel is attached in the carrier in a detachable manner (claim 19). By this means, easy cleaning and sterilization of the manipulator is ensured, because the difficult to sterilize parts of the channel become easily accessible by this means.

The drive wheel provided in the instrument designed according to the present invention can be motor-driven, by way of illustration controlled by an electronic control wheel, or driven by an operation person by hand, directly or via an intermediate gear.

With the invented instrument various instrument parts, such as tongs, scissors, laser fibers, guide wires for catheters or flexible endoscopes can be moved forward and backward. In the event the flexible endoscopes are to be handled with a flexible image conductor and a flexible illumination light conductor, it is preferred if the manipulator is provided at its distal end with a guide channel for the flexible fiber unit, which has, compared to the channel at the proximal end of the handpiece, a substantially smaller diameter.

BRIEF DESCRIPTION OF THE DRAWING

In the following, the present invention is made more apparent by way of example using preferred embodiments without the intention of limiting the scope or spirit of the overall inventive concept with reference to the drawing, depicting in:

FIGS. 1a to 1d four different cross sections preferably views of a first preferred embodiment of the present invention, and FIGS. 2a to 2d two variants of a second preferred embodiment.

DESCRIPTION OF THE PREFERRED EMBODIMENTS

Figure 1:
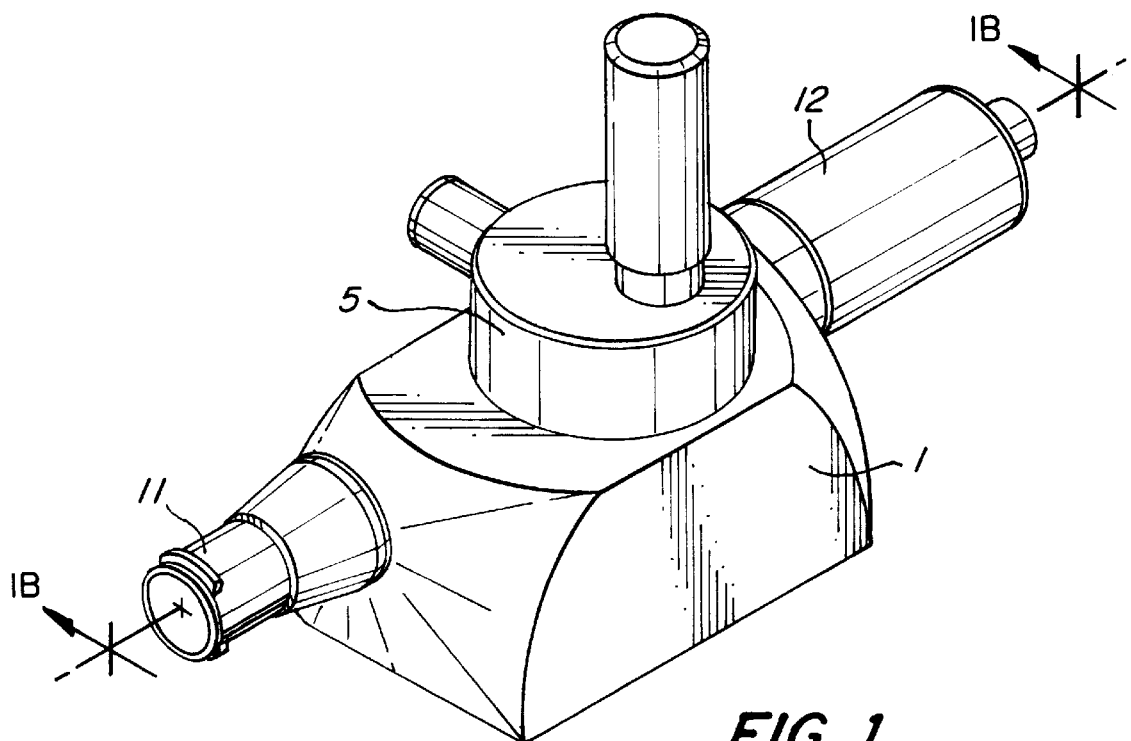
FIG. 1 an isometric view of a first preferred embodiment of the invention.

FIGS. 1a to 1d show sections A—A, B—B, C—C and D—D through the manipulator of a first preferred embodiment of the present invention.

The manipulator is provided with a basic body 1 in which a guide channel 2 is provided in which, in FIG. 1b on the left side, an instrument preferably an instrument part can be inserted and can be moved forward to the right. The instrument which, by way of illustration, can be a flexible endoscope is not shown in FIGS. 1a to 1d.

In order to move the instrument forward and backward, a drive wheel 3 and a guide wheel 4 are disposed in the guide channel 2, the perimeter of which engages with the outer contour of the not depicted instrument part.

By turning the drive wheel 3, the instrument, preferably the instrument part is moved forward and backward in direction of its longitudinal axis relative to the manipulator 1.

For adaption to the outside diameter of the to-be-moved instrument parts, the drive wheel 3 is joined to a rotatable carrier, preferably a disk 5 in such a manner that the distance between the rotation axis 5' of the disk and the rotation of axis 3' of the drive wheel 3 is unequal zero. In other words, the drive wheel 3 is attached eccentrically to the disk 5. In this way, the carrier 5 can be turned "to the left or the right" until the drive wheel 3 eccentrically attached to it contacts sufficiently firmly the respective forward and backward moving instrument, preferably instrument part located in channel 2 in such a manner that the instrument can be moved precisely without slippage.

In order to turn the drive wheel 3, the wheel is, in certain circumstances via a gear or a transmission, connected to an operation part 6 by means of which an operating person can turn the drive wheel 3 by hand.

In order to simplify cleaning, preferably sterilizing the manipulator 1 set up according to the present invention, the carrier 5 for the movable drive wheel 3 is attached in the manipulator basic body 1 in a detachable manner. In this case, a pin 7 is provided in the longitudinal axis of the latter having a profile that permits removing the carrier, preferably the disk 5 from the basic body 1 of the manipulator after moving the pin 7. An O-ring 8 is provided to seal the carrier 5 from the basic body 1. The shaft 6 of the drive wheel 3 is also inserted in a detachable manner by means of the O-ring 9.

Furthermore, the manipulator is provided on both sides of the guide channel with a standard flange, by way of illustration a Luer-lock flange 11 and a conventional endoscope flange 12, like by way of illustration the standard flange from Karl Storz GmbH & Co., Germany.

Moreover, in the region with which they engage with the outer contour of the to-be-moved instrument part, the drive wheel 3 and the guide wheel 4 are coated with a rubber-like material 3" and 4", such as by way of illustration a silicone rubber in such a manner that slippage is further minimized.

FIGS. 2a to 2d show two variants of a second preferred embodiment in which the parts corresponding to those in FIG. 1 bear the same reference numbers, thereby obviating renewed presentation.

In the second preferred embodiment, the basic body 1 is designed as a handpiece in which the channel 2 is provided for the to-be moved instrument part. The instrument part can, in particular, be a flexible thin endoscope which is transported in an extension 13 of the handpiece 1.

In the second preferred embodiment, the perimeters of the drive wheel 3 and the guide wheel 4 are provided with two O-rings 14 preferably. The wheels 3 and 4 are disposed in such a manner that in each case two O-rings are positioned opposite each other and that the O-rings enclose a gap through which the instrument, preferably the instrument part passes.

The variant shown in a longitudinal section in FIG. 2a and in a cross section in FIG. 2c in A—A differs from the variant shown in the corresponding FIGS. 2b and 2c in that in the former instance, for adapting to different instrument part diameters, two screws 15 are provided for moving the guide wheel 4, which act upon the axis 16 of the wheel 4. The axis 16 of the guide wheel 4 can be pretensioned in the opposite direction of the screwing direction of screws 15 by a not depicted spring.

In the preferred embodiment shown in FIG. 2, the drive wheel 3 is driven directly, by way of illustration using the thumb. For this reason, the drive wheel 3 has a greater diameter than the guide wheel 4.

With regard to the details not explained in more detail in the text, reference is made to the drawing without the intention of limiting for the exemplary description the scope or spirit of the overall inventive concept, as set forth in the claims.

What is claimed is:

1. A medical instrument and, in particular, an endoscopic instrument which is provided with a manipulator having a guide channel on which at least one drive wheel and at least one guide wheel preferably are disposed, the perimeter area of which can be brought to engage with the outer contour of an instrument part in such a manner that said instrument can be moved forward and backward in the direction of its longitudinal axis relative to said manipulator, characterized by for adaption to the different outside diameters of the to-be-moved instrument parts, at least one of said wheels being joined to a carrier which can be swiveled to be moveable at least in the direction perpendicular to said guide channel, the distance between a swivel axis of said carrier and the axis of rotation of said wheel is unequal zero.

2. An instrument according to claim 1, characterized by said wheels being disposed in a handpiece, which is provided with a channel for said to-be-moved instrument part.

3. An instrument according to claim 1, characterized by said manipulator being provided at least on one side of said guide channel with a standard flange for connection to said instrument.

4. An instrument according to claim 3, characterized by said standard flange being a Luer-lock flange.

5. An instrument according to claim 3, characterized by said standard flange being a conventional endoscope shaft flange and, in particular, a bayonet flange.

6. An instrument according to claim 1, characterized by said manipulator being firmly connected to a basic body of said instrument.

7. An instrument according to claim 1, characterized by said carrier for said moveable wheel being attached in a manipulator basic body in a detachable manner.

8. An instrument according to claim 1, characterized by the shaft of said drive wheel being attached in said wheel carrier in a detachable manner.

9. An instrument according to claim 1, characterized by said drive wheel being driven by hand by an operating person.

10. An instrument according to claim 1, characterized by said instrument part being an endoscope having a flexible image conductor and a flexible illumination light conductor, which are combined into a flexible fiber unit having a small diameter.

11. An endoscope according to claim 10, characterized by said manipulator being provided at its distal end with a guide channel for said flexible fiber unit, which has, compared to the channel at the proximal end of the handpiece, a substantially smaller diameter.

12. An instrument according to claim 1, characterized by said manipulator having two wheels positioned opposite each other.

13. An instrument according to claim 1, characterized by said drive wheel being coated with a rubber-like material in the region with which it engages with the outer contour of said to-be-moved instrument part.

14. An instrument according to claim 1, characterized by said carrier being a disk which can be rotated about its center axis and the axis of rotation of said moveable wheel being attached eccentrically thereon.

15. An instrument according to claim 1, characterized by said carrier having a circular outer contour in the sections perpendicular to the swivel axis and being rotatable by at least 360°, in particular, by hand.

16. An instrument according to claim 1, characterized by said drive wheel having a substantially smaller diameter than said guide wheel.

17. An instrument according to claim 1, characterized by said drive wheel having a substantially smaller diameter than said at least one guide wheel.

18. An instrument according to claim 1, characterized by said wheel being disposed in a handpiece, which is provided with a channel for said to-be-moved instrument part.

19. An instrument according to claim 1, characterized by said carrier for said moveable wheel being attached in a manipulator basic body in a detachable manner.

20. An instrument according to claim 1, characterized by the shaft of said drive wheel being attached in said wheel carrier in a detachable manner.

21. A medical instrument which is provided with a manipulator having a guide channel on which at least one drive wheel and at least one guide wheel are disposed, the perimeter area of which can be brought to engage with the outer contour of an instrument part in such a manner that said instrument part can be moved forward and backward in the direction of its longitudinal axis relative to said manipulator, characterized by for adaption to the different outside diameters of the to-be-moved instrument parts, at least one of said wheels being provided with an elastic coating on its outer contour and one of said wheels being provided with two screws which act upon the axis of said wheel to move it, the axis of said moveable wheel being pretensioned by a spring in the opposite direction of the screwing in direction.

22. An instrument according to claim 21, characterized by said manipulator having two wheels positioned opposite each other.

23. An instrument according to claim 21, characterized by one said drive wheel being coated with a rubber-like material in the region with which it engages with the outer contour of said to-be-moved instrument part.

24. An instrument according to claim 23 characterized by said rubber-like material being a silicone rubber.

25. An instrument according to claim 23, characterized by the perimeters of said wheels being provided with two O-rings and by said wheels being disposed in such a manner that two O-rings are positioned opposite each other respectively, and by said O-rings enclosing a gap through which said instrument part passes.

26. An instrument according to claim 21 characterized by said moveable wheel for adaption to different instrument diameters being said drive wheel.

* * * * *